United States Patent [19]
Parker et al.

[11] Patent Number: 5,902,728
[45] Date of Patent: *May 11, 1999

[54] DIAZODENITRIFICATION IN MANUFACTURE OF RECOMBINANT BACTERIAL BIOSENSORS

[75] Inventors: Jill E. Parker, San Antonio; John L. Alls, Brooks AFB; Jonathan L. Kiel, Universal City, all of Tex.

[73] Assignee: The United States of America as represented by the Secretary of the Air Force, Washington, D.C.

[ * ] Notice: This patent is subject to a terminal disclaimer.

[21] Appl. No.: 08/933,561

[22] Filed: Sep. 19, 1997

Related U.S. Application Data

[63] Continuation-in-part of application No. 07/779,694, Oct. 21, 1991.

[51] Int. Cl.⁶ .............................. C12Q 1/02; C12N 15/70
[52] U.S. Cl. .................... 435/7.37; 435/6; 435/172.3; 435/183; 435/252.3; 435/252.33; 435/320.1; 536/23.2; 536/23.7
[58] Field of Search .................. 435/172.3, 183, 435/252.3, 252.33, 320.1, 6, 7.37; 536/23.2, 23.7, 23.1

[56] References Cited

U.S. PATENT DOCUMENTS

| | | | |
|---|---|---|---|
| 5,003,050 | 3/1991 | Kiel et al. | 534/573 |
| 5,156,971 | 10/1992 | Kiel et al. | 435/252.31 |
| 5,464,768 | 11/1995 | Kiel et al. | 435/355 |

FOREIGN PATENT DOCUMENTS 227 909  8/1987  European Pat. Off. .

OTHER PUBLICATIONS

Maniatis et al. CSH Labs "Molecular Cloning", 1982.
ATCC Catalogue of Recombinat DNA Materials (Vectors), p. 36, 1991.
ATCC Catalogue of Bacteria & Phages (Bacteria), p. 97, 1989.
Gene 32 pp. 481–485, Lawrence et al., 1984.

Primary Examiner—John L. LeGuyader
Attorney, Agent, or Firm—Charles E. Bricker; Thomas L. Kundert

[57] ABSTRACT

*E. coli* strain JM109 transfected with nitrate reductase gene containing plasmid pIC20RNR1.1 produces diazoluminomelanin when cultured in a medium containing nitrate, 3-amino-L-tyrosine and luminol, under suitable metabolic conditions.

3 Claims, 10 Drawing Sheets

COLONY FORMING UNITS

KEY: ○ BLOOD AGAR
□ AMPILLICIN AGAR log dilution of 1 mg/ml 2-chloroethyl ethyl sulfide

*Fig. 8*

DIAZODENITRIFICATION IN MANUFACTURE OF RECOMBINANT BACTERIAL BIOSENSORS

This application is a continuation-in-part of application Ser. No. 07/779,694, filed Oct. 21, 1991.

RIGHTS OF THE GOVERNMENT

The invention described herein may be manufactured and used by or for the Government of the United States for all governmental purposes without the payment of any royalty.

BACKGROUND OF THE INVENTION

This invention relates to luminescent reagents.

Specific binding assays provide an economical means for detecting and measuring an analyte present in low concentrations in a sample. Specific binding assays are based upon the interaction of two bindable substances, one the analyte and the other a specific binding partner, which specifically recognize each other. Examples of specific binding partners whose interaction can serve as the basis for a specific binding assay include antigens-antibodies, biotin-avidin, nucleic acid probes, enzymes-substrates, enzymes-inhibitors, enzymes-cofactors, chelators-chelates, and cell surface receptor pairs. Assays involving other specifically bindable substances are also known and within the scope of the present invention. Specific binding assays have shown great utility in determining various analytes in biological, medical, environmental, agriculture and industrial applications.

A variety of assays using the principles of the specific binding approach are known, and several have become important diagnostic tools. In one such type of specific binding assay, the immunoassay, the analyte is an antibody, antigen, or hapten, and is made to react with another member of this group. While the background discussion will focus on such immunoassays, this focus is made for clarity of presentation, and is not to be interpreted as limiting of the invention.

A variety of labeling reactions have been proposed for use in specific binding assays, including radioactive, enzymatic, chromogenic and luminogenic procedures. In a radioactive labeling procedure, the component conjugated with the specific binding partner is an atom or molecule which emits radioactivity. Chromogenic and luminogenic labeling reactions are chemically more complex, in that several reactants may be involved. The chromophore or lumiphore may itself be the label in the reaction, or a catalyst, typically an enzyme, may be used as the label. When the catalyst is used as the label, it will react with catalytic substrates which in turn produce color or luminescence. The remaining components of the reaction, that is, those not conjugated to the binding partner, are supplied in a chromogenic or luminogenic reagent medium, so that the uniting of the labeled conjugate and the reagent medium results in the desired color change or light emission, respectively.

Luminescent labels are attractive alternatives for use in specific binding assays for a variety of reasons. Luminescence is broadly defined as the production of visible light by atoms that have been excited by the energy produced in a chemical reaction, usually without an associated production of heat. Chemical energy excites electrons in the light-emitting molecules to higher energy states, from which electrons eventually fall to lower energy states with the emission of quanta of energy in the form of visible light. Luminescence is observed in several synthetic chemical compounds and also in naturally occurring biological compounds such as found in fireflies and certain varieties of fish.

One of the most important families of chemiluminescent molecules are the phthalylhydrazides. The most familiar member of this family is luminol, or 5-amino-2,3-dihydro-1,4-phthalazinedione, which has a gross chemical composition of $C_8H_7N_3O_2$ and a double ring structure with a melting point of about 320° C. Luminol is commercially available from several suppliers and is well characterized. Certain luminol analogs are also chemiluminescent, such as those wherein the position of the amino group is shifted (e.g., isoluminol, the amino group being at the 6 position), or is replaced by other substituents, as well as annelated derivatives and those with substitution in the nonheterocyclic ring. Some luminol analogs produce light more efficiently than does luminol itself, while others have lower efficiency. (As used herein, the term "luminol" encompasses such related species.)

Generally, luminol produces light in an oxidizing reaction, wherein the luminol combines with oxygen or an oxidizer to produce a reaction product and photons at a wavelength of about 425–450 nanometers (nm). The precise reaction formula and the quantum efficiency of light production, i.e., the ratio of luminescing molecules to total molecules of the luminescent species, depend upon the medium in which the luminol resides, temperature and other reaction conditions. Typical oxidizers used in conjunction with luminol include oxygen, hydrogen peroxide, hypochlorite, iodine and permanganate.

The oxidation of luminol with the associated production of light occurs rather slowly at ambient temperatures, unless the reaction is catalyzed. A variety of different substances can catalyze the reaction, including organic enzymes, e.g., horseradish peroxidase, other organic molecules such as microperoxidase and heme, positive metallic ions such as the cupric ion, and negative ions such as the ferricyanate ion.

Luminescent molecules would appear to be highly desirable as tags in specific binding assays because of their stability, sensitivity, the potential ease of detecting their emitted visible light and their lack of toxicity. Commercial luminol, however, has proven to be unsuitable for such purposes. There exists a need for specific improvements in the light emission characteristics of the reaction for use with such assays. Heretofore, commercial luminol has not shown sufficient activity to be useful to measure analytes at low concentrations in specific binding assays. The light emission intensity of the luminol reaction may be sufficient where high concentrations of catalyst are employed and where highly sophisticated and sensitive photometers are available, but the luminescent intensity has not been sufficient with low concentrations of catalyst and where other detection media such as photographic film or less sensitive photometers are used.

While the luminol reaction therefore offers important potential benefits in the measurement of the presence and amount of a reaction component, for many potential applications, the intensity of the emitted light is too low. Further, the light emitted from commercial luminol exhibits an early flash of light within the first few seconds of the initiation of the reaction, followed by a progressive and rapid decrease in light emission over time. The integrated light intensity during any fixed period of time is therefore likely to be different from that measured over any other equal period of time. This variability may result in irreproducibility between tests. Desirably, there would be some period of time during which the light emission from the luminol reaction is relatively constant, so that the measurement of integrated light intensity could begin at different times after initiation of the reaction, but within the period of constant light output, without variability of the results. This would eliminate the requirement that the reagents be added to a solution fixed in front of the luminescence detector which puts severe constraints on the light measuring system.

Higgins et al, U.S. Pat. No. 4,743,541, disclose that the intensity and duration of emitted light from luminol can be considerably improved by repeatedly dissolving and recrystallizing the luminol until sulphide and hydrazine levels are below about 100 ppm.

The production of chemiluminescence with luminol comprises dissolving the luminol in an organic solvent, such as DMSO or acetone, or in a strong base and diluting the solution in a buffer of desired pH. The amount of luminol that can be dissolved is severely limited by the relative insolubility of luminol in water at a pH below 10.

When luminol is covalently attached to carriers such as protein, its chemiluminescence is quenched. Isoluminol, although less efficient in light production than luminol, is quenched to a lesser degree by covalent attachment. The noncovalent attachment of luminol to bovine serum albumin prevents quenching and solubility problems, but "leaks" luminol into the solution by forming an equilibrium between bound and unbound luminol, thus decreasing the specificity of luminol/carrier dependent immunoassays and enzyme-linked assays.

There is a need for a luminescent probe which is water soluble, is highly quantum efficient, and provides long-lived chemiluminescence.

U.S. Pat. No. 5,003,050, issued Mar. 26, 1991, to Johnathan L. Kiel and Gerald J. O'Brien, discloses a water-soluble luminescent compound having repeating units of the formula:

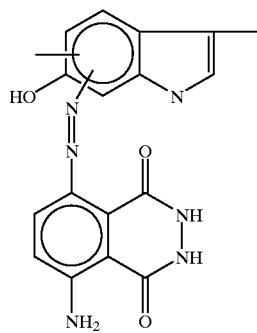

The product, which is a polymer having repeating units comprising diazo-linked luminol and hydroxyindole, is referred to as diazoluminomelanin (DALM), since one of the precursors to this product, 3-amino-L-tyrosine (3AT) is closely related to the biological substrates which are converted into melanin.

DALM is water soluble, having an apparent pKa for solubility about pH 5.0. DALM does not require a catalyst for chemiluminescence. The duration of the reaction is in excess of 52 hours. In contrast, luminol requires a catalyst; with microperoxidase as the catalyst, luminol has shown peak luminescence at 1 sec and half-lives of light emission of 0.5 and 4.5 sec at pH 8.6 and 12.6, respectively. The chemiluminescence yield of DALM is better at pH 7.4 than at pH 9.5, although it still provides a strong signal at strongly basic pHs. DALM also produces chemiluminescence at pH 6.5 which is about the same intensity as that produced at pH 9.5.

DALM can be used for chemiluminescent immunoassays for biological and chemical agents; in radiofrequency and ionizing radiation dosimeters; and for RNA/DNA hybridization assays for viruses and genetic detection.

Also disclosed in U.S. Pat. No. 5,003,050 is a method for preparing DALM which comprises reacting 3AT with an alkali metal nitrite, and reacting the resulting diazonium salt with luminol. The method involves the use of organic solvents such as dimethylsulfoxide and acetone. On a large scale, handling and disposal of such solvents could be both dangerous and difficult.

We have discovered that a particular strain of *Escherichia coli* bacteria containing a plasmid constructed with a barley nitrate reductase gene fragment, grown on a nitrate/luminol/3-amino-L-tyrosine medium produces large quantities of DALM. Additionally, the *E. coli* containing the recombinant DNA plasmid can be employed for the purpose of detecting physical, chemical and/or radiation stressors.

Accordingly, it is an object of the present invention to provide an improved biosynthetic method for producing DALM.

Another object of the present invention is to provide methods for detecting physical, chemical and/or radiation stressors.

Other objects, aspects and advantages of the present invention will be apparent to those skilled in the art from a reading of the following detailed disclosure of the invention.

SUMMARY OF THE INVENTION

In accordance with one aspect of the present invention there is provided a method for producing diazoluminomelanin (DALM) which comprises culturing in a medium containing nitrate, 3-amino-L-tyrosine (3-AT) and luminol under suitable metabolic conditions, a microorganism containing a plasmid constructed with a barley nitrate reductase gene fragment.

In accordance with a second aspect of the present invention there is provided an improved method for producing diazoluminomelanin (DALM) which comprises culturing in a medium containing nitrate, 3-amino-L-tyrosine (3-AT) and luminol under suitable metabolic conditions, *E. coli* strain JM109 transfected with nitrate reductase gene containing plasmid pIC20RNR1.1.

Also provided in accordance with this second aspect of the present invention are methods for detecting physical, chemical and/or radiation stressors.

BRIEF DESCRIPTION OF THE DRAWINGS

In the drawings,

FIGS. 8–10 illustrate the use of *E.coli* JM109/pIC20RNR1.1 in a mutagenic assay.

DETAILED DESCRIPTION OF THE INVENTION

Figure 1:
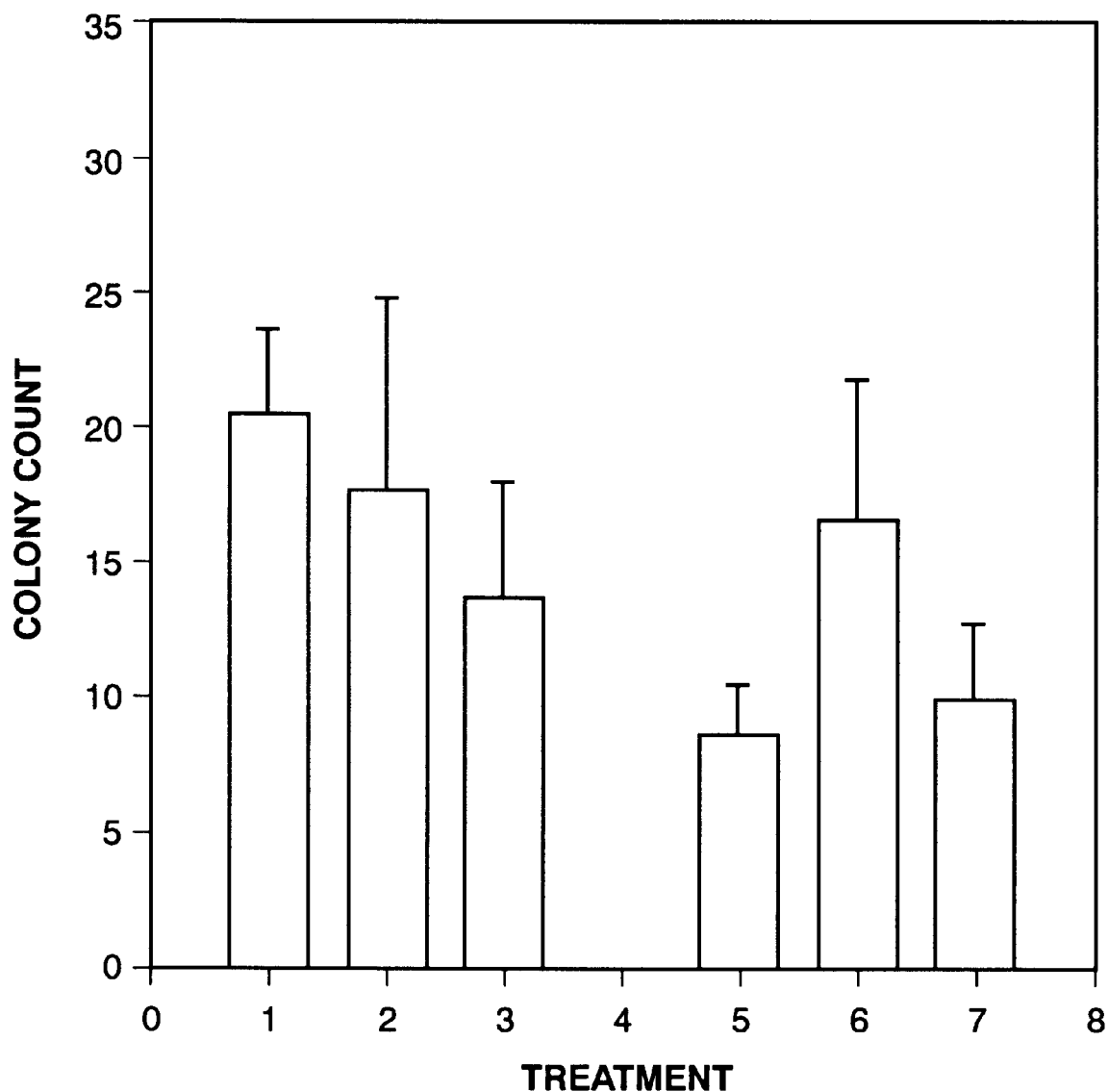
FIG. 1 illustrates the effects of Ultrawide Band Radiation on *E.coli* JM109/pIC20RNR1.1.

The microorganisms which may be employed in accordance with the invention include all organisms containing nitrate reductase, i.e., those inherently containing nitrate reductase and those into which nitrate reductase can be introduced by recombinant DNA technology. Nitrate reductase is found in several strains of *Escherichia coli* (*E. coli*), salmonella, fungi such as, for example, *Neurospora crassa*, algae such as, for example, *Chlamydomonas reinhardtii*, denitrifying bacteria such as, for example, *Micrococcus denitrificans*, and higher plants. The gene for nitrate reductase has been cloned and can be transferred in expression vectors such a plasmids and bacteriophages.

The culture medium must be suitable for the microorganism employed. Nitrate, 3-AT and, optionally, luminol, as noted previously, are added to the medium. 3-AT exhibits bacteriostatic properties; accordingly, it may be necessary to carry out some experimentation to determine the maximum and desired levels of 3-AT.

The conditions for culturing the microorganisms will vary depending upon the microorganism under investigation. For example, we found that certain strains of *E. coli* without tyrosinase require nitrate reducing conditions followed by aerobic conditions, while other microorganisms produced 2,4-DALM under aerobic conditions. In the first case, the microorganisms are grown under anaerobic to microaerophillic conditions to optimize production of nitrite and, subsequently, diazotyrosine. The medium is then oxygenated to facilitate conversion of diazotyrosine to diazomelanin (DM). When luminol is present, the same procedure is followed yielding diazotyrosine and diazoluminol which react to form diazoluminomelanin.

Activation of DM and DALM is accomplished by mixing the culture with a suitable base and hydrogen peroxide and reading the resulting luminescence.

Diazomelanin (DM) and diazoluminomelanin (DALM) can be used in producing thermochemiluminescent radiofrequency radiation microdosimeters. They can also be used as ultraviolet light absorbers, microwave and radiofrequency radiation absorbers, cation exchangers, bioelectrodes, semiconductors and drug-binding biopolymers. In addition, when DM and DALM are produced intracellularly, they can link by diazocoupling and alkylation to nucleic acids and proteins produced by the microorganisms. Transferred nucleic acids and proteins from cloned genes can be produced and labeled with the luminescent polymers in the microorganisms as part of the same process. These labeled products can then be recovered and purified for their ultimate use as diagnostic probes and therapeutic agents. Examples of labeled proteins include immunoglobulins, enzymes, receptor proteins, nucleic acid binding proteins, and specific protein binding proteins. Such labeled probes may be used therapeutically to target unwanted genetic material, viral genomes and whole viruses, pathogenic bacteria, fungi, protozoans, parasites and tumor cells for destruction by free radical reactions and heating by microwave and radiofrequency radiation absorption mediated by the DM or DALM.

In particular, *E. coli* strain JM109, containing plasmid pIC20RNR1.1, produces improved quantities of DALM. The plasmid pIC20RNR1.1 was constructed by insertion of the 1.1 kilobase fragment of the barley plant nitrate reductase gene, originally obtained from Massachusetts General Hospital, Boston, Mass., into the cloning site Pst1 of the pIC20R plasmid (American Type Culture Collection No. 37381). The cells were transfected with the barley nitrate reductase gene by electroporation in accordance with known procedures. The *E. coli* strain JM109, containing plasmid pIC20RNR1.1, has been deposited with the American Type Culture Collection and has been designated No. 69905.

The JM109/pIC20RNR1.1 cells were grown in 2X3AT broth which contained 30 g dehydrated trypticase soy broth, 12 g potassium nitrate, 100 mg luminol and 320 mg 3-amino-L-tyrosine HCl dissolved in 1 liter of water and filter sterilized or autoclaved. The cells were also grown in 4X3AT broth which contained twice as much potassium nitrate, luminol and 3AT as the 2X3AT broth per liter (and so forth for higher X's).

The cultures were grown in screw top sterile culture tubes for 24 hrs at 37° C. in a bacterial incubator. When grown for production of DALM, the bacteria were grown up to two weeks in 1 liter or greater flasks in a rotary incubator.

Following growth for sensitivity testing, the cells were washed in phosphate-buffered saline (PBS), exposed in trypticase soy broth (TSB) and transferred to trypticase soy agar (TSA) or blood agar for colony counts after being diluted in either PBS or TSB for serial dilutions for the counts. When various species and strains of bacteria were being tested for diazodenitrification of 3AT and luminol (the process of DALM formation), comparative luminescence studies were performed with controls grown on 2,4-dichlorophenol (320 mg/liter) substituted for the 3AT or 3-nitro-L-tyrosine (320 mg/liter) substituted for the 3AT and nitrate in the 2X3AT agar. At time of exposure to a challenging agent, the bacteria loaded with DALM are activated with sodium carbonate or bicarbonate and hydrogen peroxide to enhance sensitivity. Varying the concentration of the 3AT medium (2X, 4X, etc) for the 24 hr growth period also varied sensitivity.

Table I shows comparative results of DALM production measured by thermochemiluminescence (at 45° C.) of various strains and species of bacteria suspended in 50 microliters of PBS and activated with 100 microliters of 0.3M sodium bicarbonate and 100 microliters of 3% hydrogen peroxide. The luminescence is in relative light units measured for 30 sec in a Turner 20e luminometer. The bacteria that showed the greatest production of DALM in the 24 hr period and the greatest diazodenitrification (shown by the 3-nitro-L-tyrosine thermochemiluminescence) was *Escherichia coli* JM109 containing the recombinant DNA plasmid pIC20RNR1.1. Data from the parent bacterial strain are also shown in Table I. Growth medium containing ampicillin was used to select for bacteria successfully transfected with the plasmid.

TABLE I

Slow Luminescence of Nitrogen-metabolizing Bacteria

| Species | Medium | | | | | |
| --- | --- | --- | --- | --- | --- | --- |
| | TSA | 2X3AT | 3-NitroT | 2,4-DCP | NR | $N_2$ |
| *Bacillus Anthracis* | 20.3 | 39.0 | 22.1 | 13.3 | + | − |
| *Bacillus cereus* | 52.6 | 184.6 | 25.7 | 33.6 | + | − |
| *E.coli* JM109/ pIC20RNR1.1 | 46.1 | 860.0 | 142.1 | 58.9 | + | − |
| *E.coli* JM109 | 75.0 | 199.0 | 12.9 | 61.6 | + | − |

In the above table: NR means nitrate reduction; TSA means trypticase soy medium; 2X3AT is as previously defined; 3-NitroT means 3-nitro-L-tyrosine/luminol medium; 2,4-DCP means 2,4-dichlorophenol/luminol/nitrate medium.

Examination of the data in Table I clearly shows the greatly enhanced production of DALM in *E.coli* JM109/pIC20RNR1.1 when grown in 2X3AT.

Referring to the drawings, FIG. 1 shows the results of Ultrawide Band Radiation (UWB) effects on *E. coli* JM109/ pIC20RNR1.1 grown for 24 hr on 4X3AT, washed in PBS and treated. The activated cells were exposed in trypticase soy broth containing 7.5 mg/ml sodium bicarbonate and 0.0003% hydrogen peroxide for a total of 30 min including 2 min exposure to UWB for 2 min, 2 sec on and 2 sec off in E-field polarization with a 300 picosec rise time, 1 kHz pulse repetition frequency, 21 kV/m field and 6 nanosec pulse width. The treatments shown are as follows: 1-not activated, UWB exposed for 2 min; 2-not activated, sham exposure; 3-not activated, 40.2° C. for 30 min; 5-activated with peroxide and sodium bicarbonate, UWB exposed for 2 min; 6-activated, sham exposure; 7-activated, 40.8° C. for 30 min.

Figure 2:
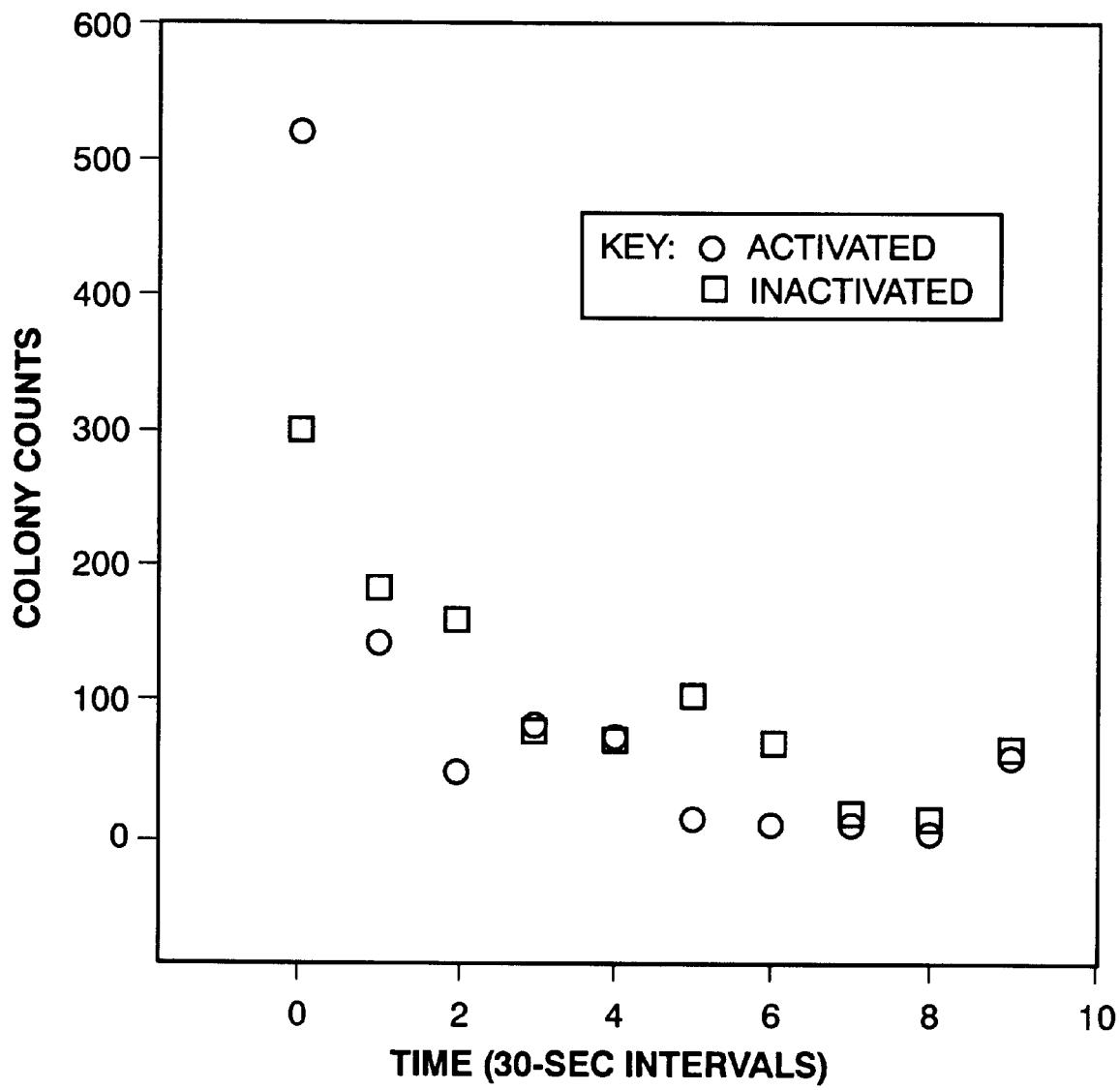
FIG. 2 illustrates the sensitivity of *E.coli* JM109/pIC20RNR1.1 grown on 2X3AT medium to ultraviolet radiation with and without activation.
Figure 3:
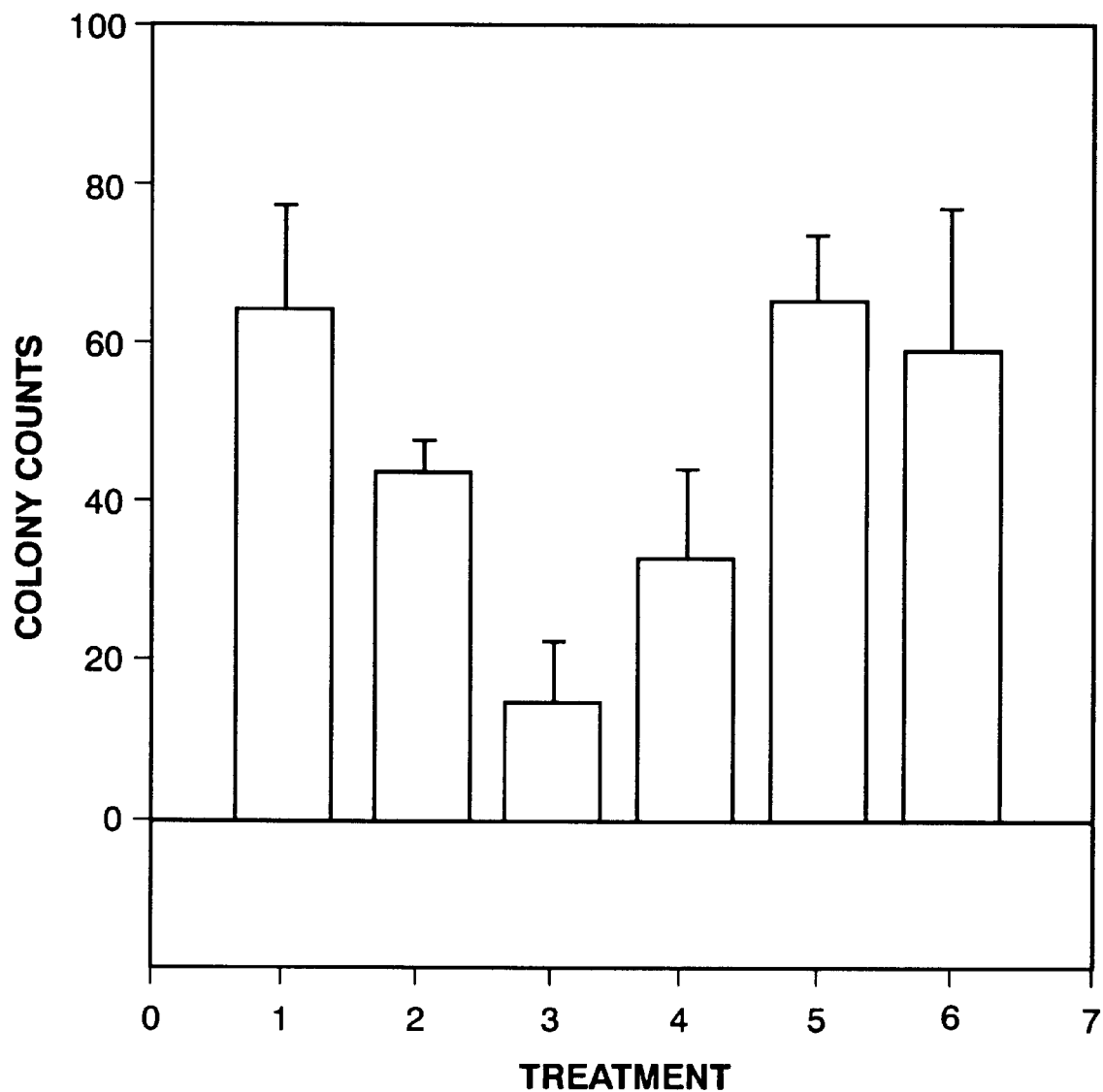
FIG. 3 illustrates the sensitivity of *E.coli* JM109/pIC20RNR1.1 grown on 2X3AT medium to ultraviolet radiation compared to the same organism grown on TSB.

FIG. 2 shows the results of the UVB (peak at 300 nm wavelength) exposures (at lowest setting of a Fotodyne DNA analytical transilluminator; 15 watt bulb, requires over 20 min to produce detectable DNA damage at this setting) of JM109/pIC20RNR1.1 *E. coli* grown on 2X3AT medium and exposed in TSB. Activated (○) vs. Inactivated (□) means treated with 0.0003% hydrogen peroxide and sodium bicarbonate (7.5 mg/ml) during exposure or not. In this case, it made little difference. FIG. 3 illustrates the survival of activated bacteria of this strain grown on TSB (□) as compared to growth on 2X3AT (○). Half survival for the DALM-loaded bacteria was less than 30 sec as compared to 4 to 4.5 min. for those without DALM. FIGS. 2 and 3 clearly show that these DALM-loaded bacteria can be used to determine response to a stressor. Following exposure of a known quantity of DALM-loaded bacteria to a stressor, such as UVB or other non-ionizing radiation, the surviving quantity is indicative of the level of exposure.

Figure 4:
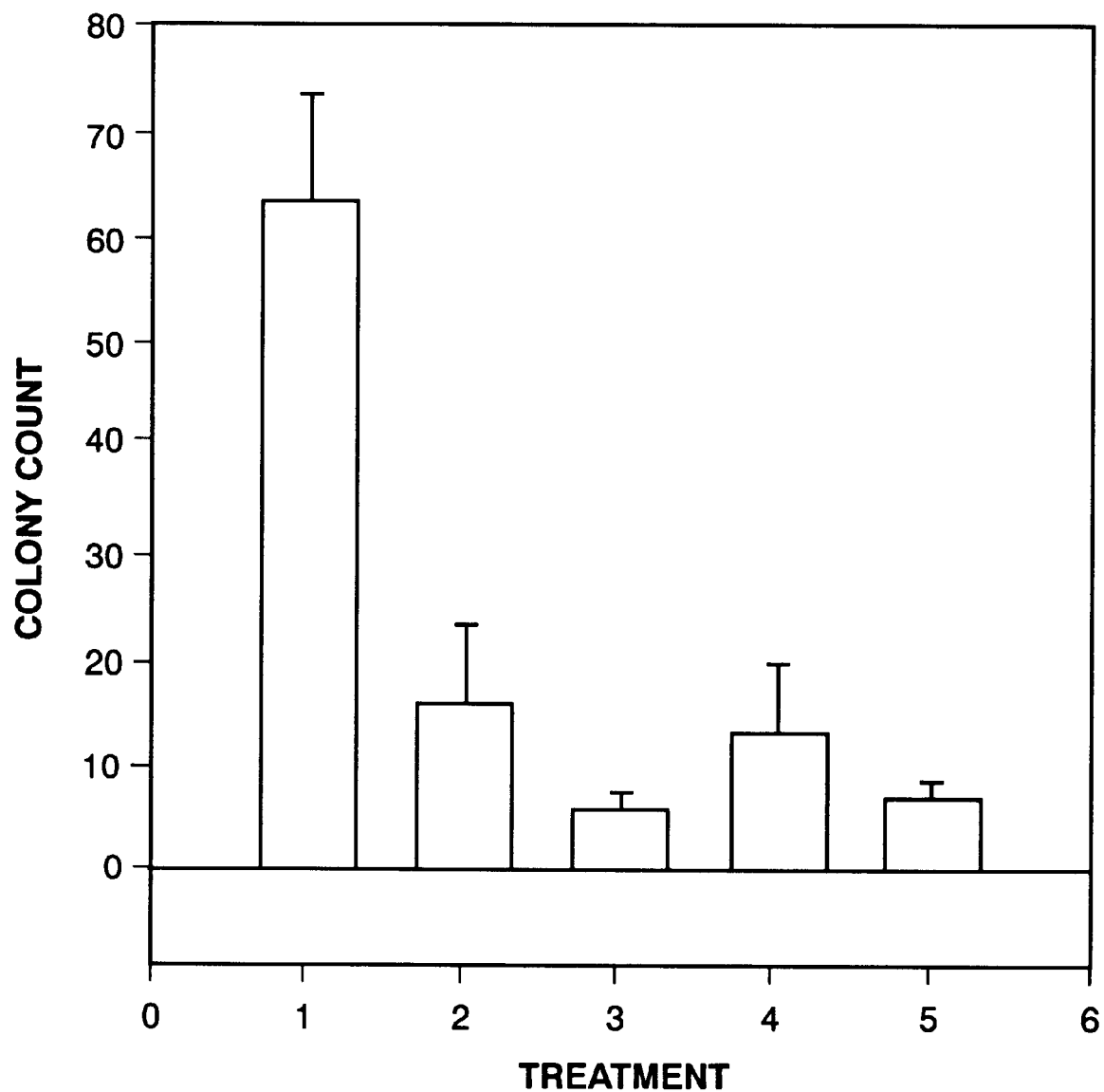
FIGS. 4–7 illustrates the behavior of *E.coli* JM109/pIC20RNR1.1 under a variety of growth and treatment conditions.

FIG. 4 shows the sensitivity of the activated bacteria to ultrawide band exposure (see above) and to conventional heat (42° C. for 30 min) with and without ampicillin (which, in general, decreased the survivability of the transfectants, although they are resistant to ampicillin; enhanced killing effects of DALM). The treatments were as follows: 1-sham; 2-42° C. for 30 min; 3-UWB exposure for 2 min followed by culture on TSA containing ampicillin; 4-sham grown on ampicillin-containing medium; 5-42° C. for 30 min followed by growth on ampicillin-containing medium.

Figure 5:
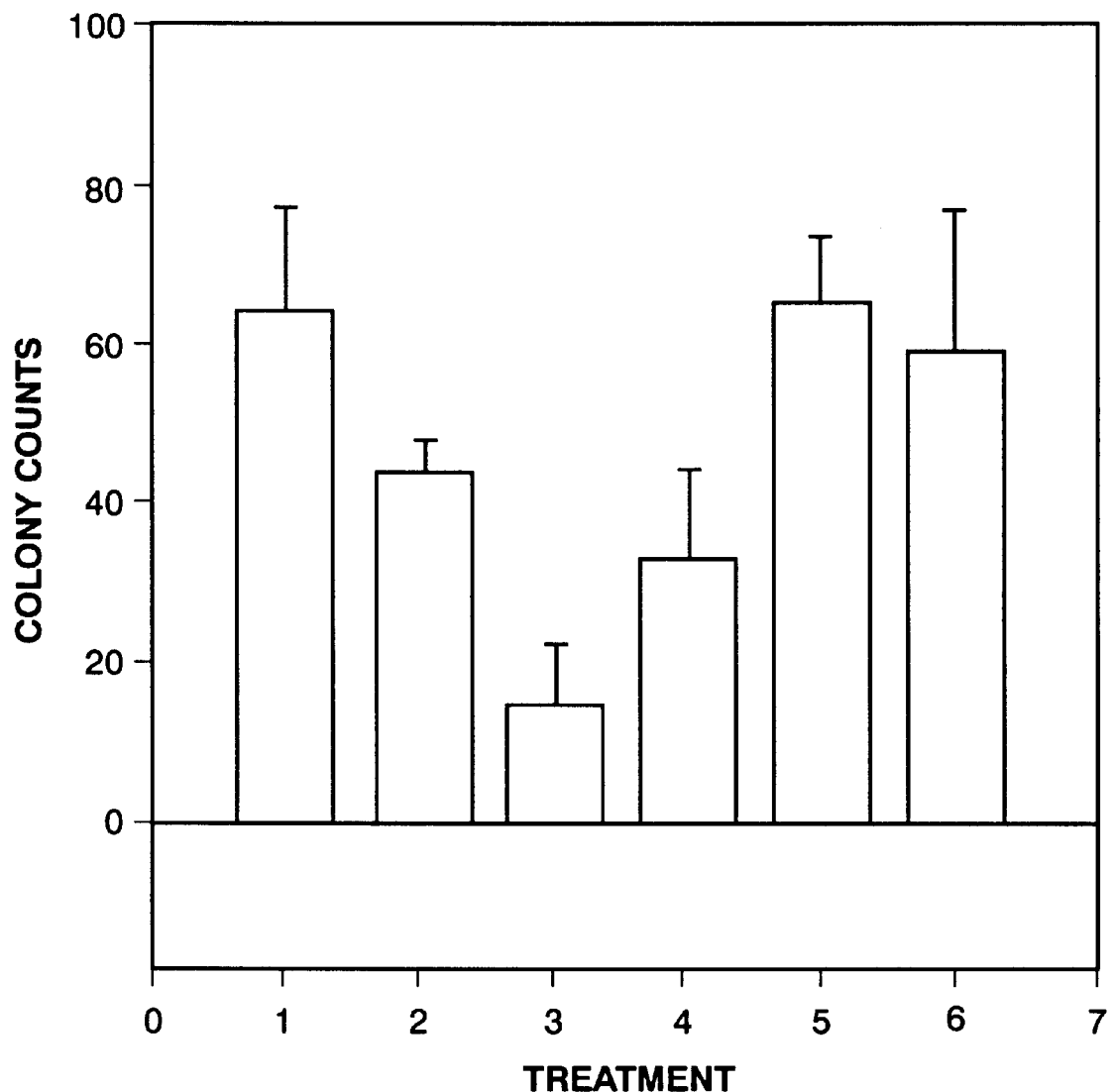

FIG. 5 shows that the results of elevated temperature in these sensitized bacteria are consistent (45° C.). *E. coli* can normally tolerate and grow at temperatures from 15° to 45° C. and are killed at 60° C. after 30 min of exposure. However, the effects of UWB radiation and ampicillin with cells containing activated DALM may be significant but reversed or neutralized. The treatments were as follows: 1-exposed to UWB for 2 min; 2-sham; 3-45.4° C. for 30 min; 4-45.4° C. for 30 min grown on ampicillin-containing medium for colony counts; 5-UWB exposed followed by growth on ampicillin-containing medium; 6-sham, followed by growth on ampicillin-containing medium.

Thus, DALM can be produced in large amounts consistently in a recombinant DNA containing *E. coli* and the toxicity controlled. When these cultures are cyclically frozen (−20° C.) and thawed, the DALM separates into a supercooled liquid fraction. Upon pooling of these fractions from several tubes and cycles, they become totally refractory to freezing at −20° C. and freeze at −40° C. after 30 min. The fractions are very dark brown to black and show strong slow thermoluminescence and fluorescence. They also bind covalently to epoxy polymer and show slow fluorescence as does chemically synthetic DALM. The DALM and its components purified through the cyclic process supersaturate the solution and precipitate as crystals of monomer and precursor and "sea urchin" spiny crystals (radial).

Figure 6:
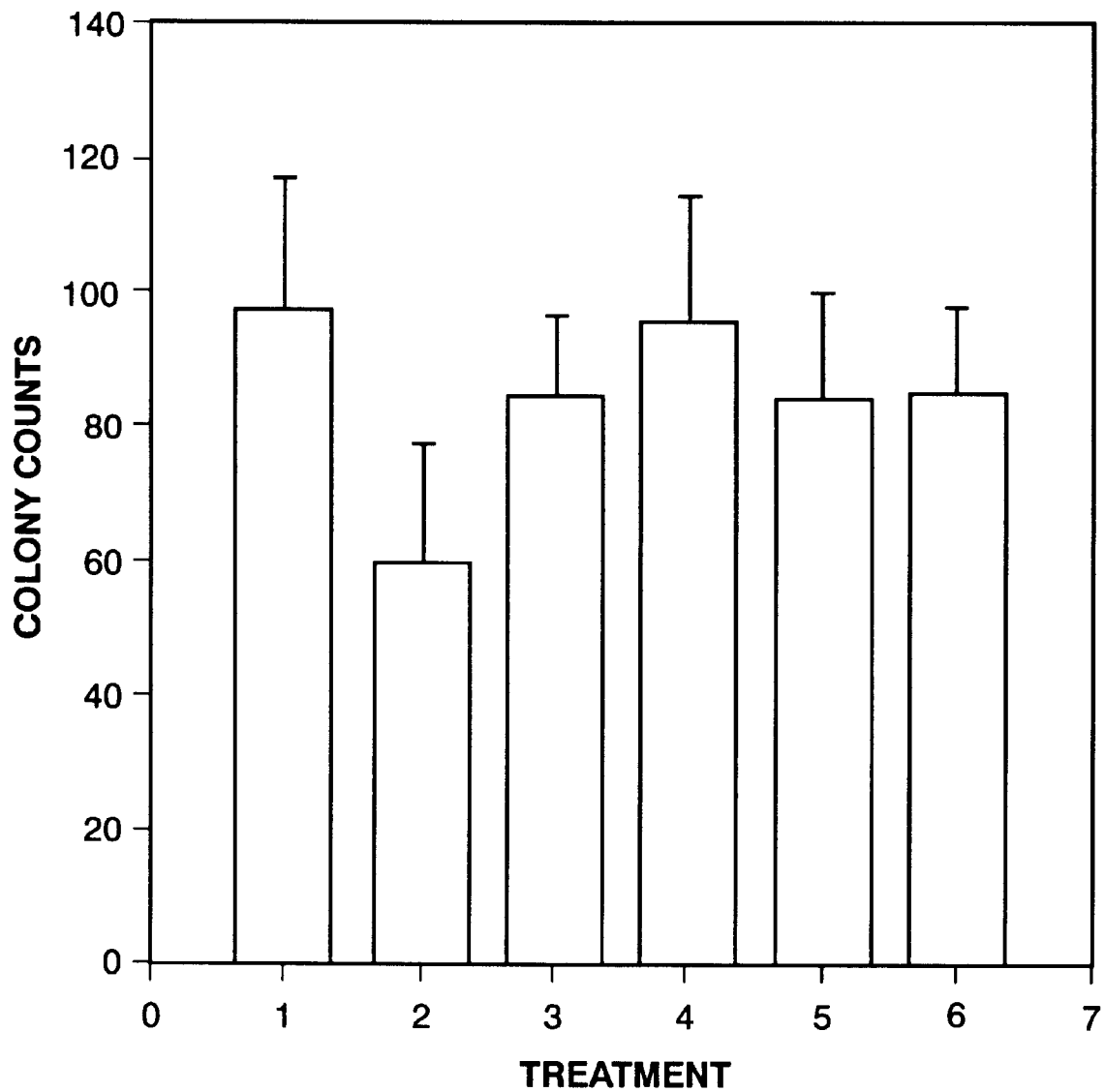

The bacteria sensitized by DALM formation and activation that responds to UWB radiation can be protected from a response by shielding against light exposure, but not UWB radiation. These machines put out radiation other than UWB, including visible and UV light from the spark gaps and plasmas they generate. FIG. 6 is an example of such a shielded response. In FIG. 6, the JM109/pIC20RNR1.1 *E. coli* were grown on 2X3AT medium, activated and treated as follows: 1-UWB exposure for 2 min; 2-UWB exposure for 2 min but shielded from light; 3-sham; 4-UWB exposure for 2 min followed by growth on ampicillin-containing medium for colony counts; 5-UWB exposure but shielded from light followed by growth on ampicillin-containing medium for colony counts; 6-sham grown on ampicillin medium.

Figure 7:
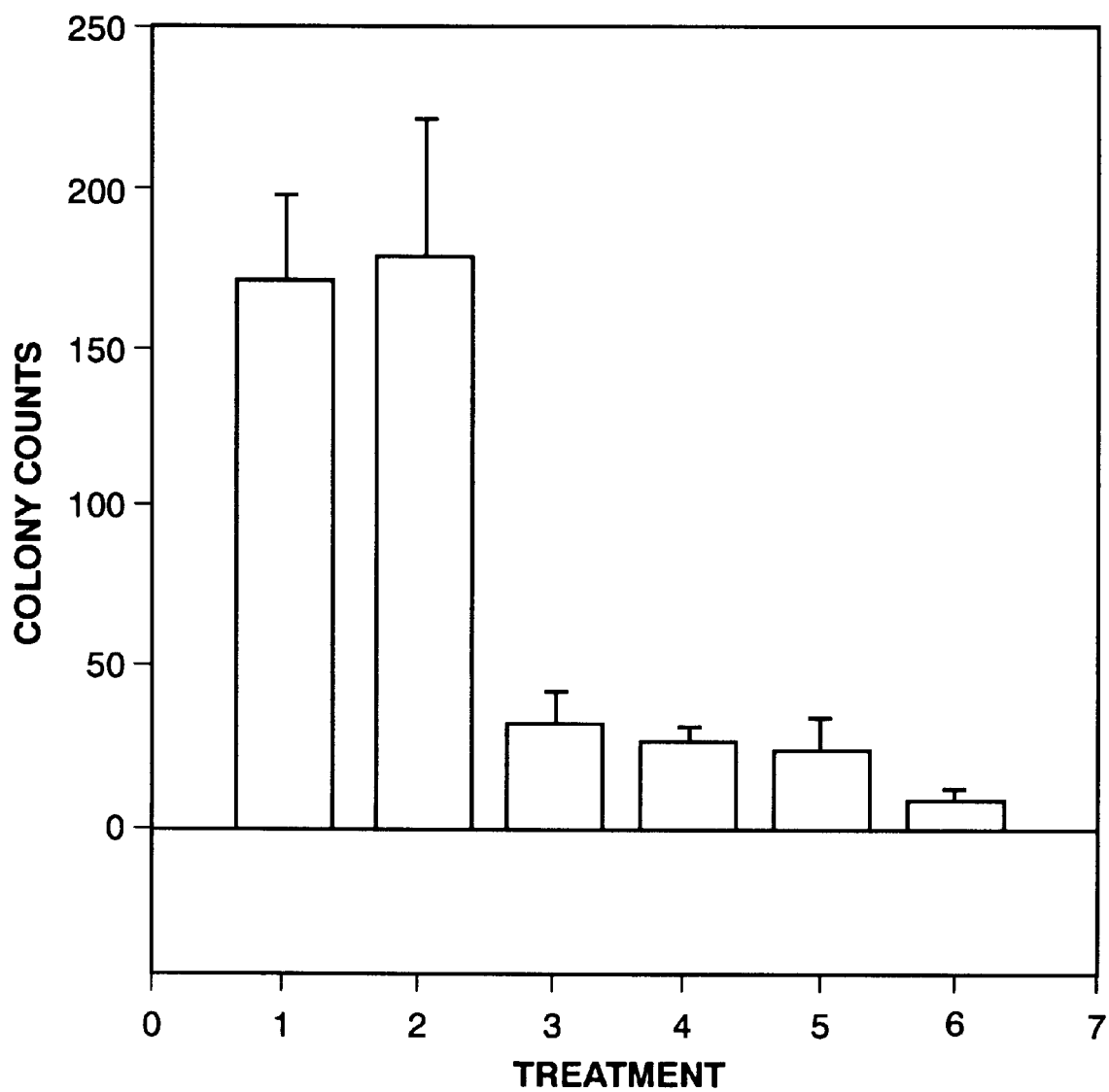

Lactose (0.5%), when added to the 2x3AT medium, decreases the variability in survival data and sharpens effects of heat and ampicillin on the sensitized bacteria (in the negative direction for ampicillin) and dispels the UWB effect. The lactose interactions can be seen in FIG. 7, wherein the JM109/pIC20RNR1.1 *E. coli* were grown on 2X3AT medium, activated and treated as follows: 1-UWB exposure for 2 min; 2-sham; 3-45.2° C. for 30 min; 4-UWB exposure followed by growth on ampicillin-containing medium for colony counts; 5-sham grown on ampicillin medium; 6-45° C. for 30 min followed by growth on ampicillin-containing medium. This is an example how the responses of the recombinant bacteria can be adjusted (increased sensitivity in one respect and decreased sensitivity in another). The lactose drives expression of the pIC20NR1.1 plasmid.

Figure 9:
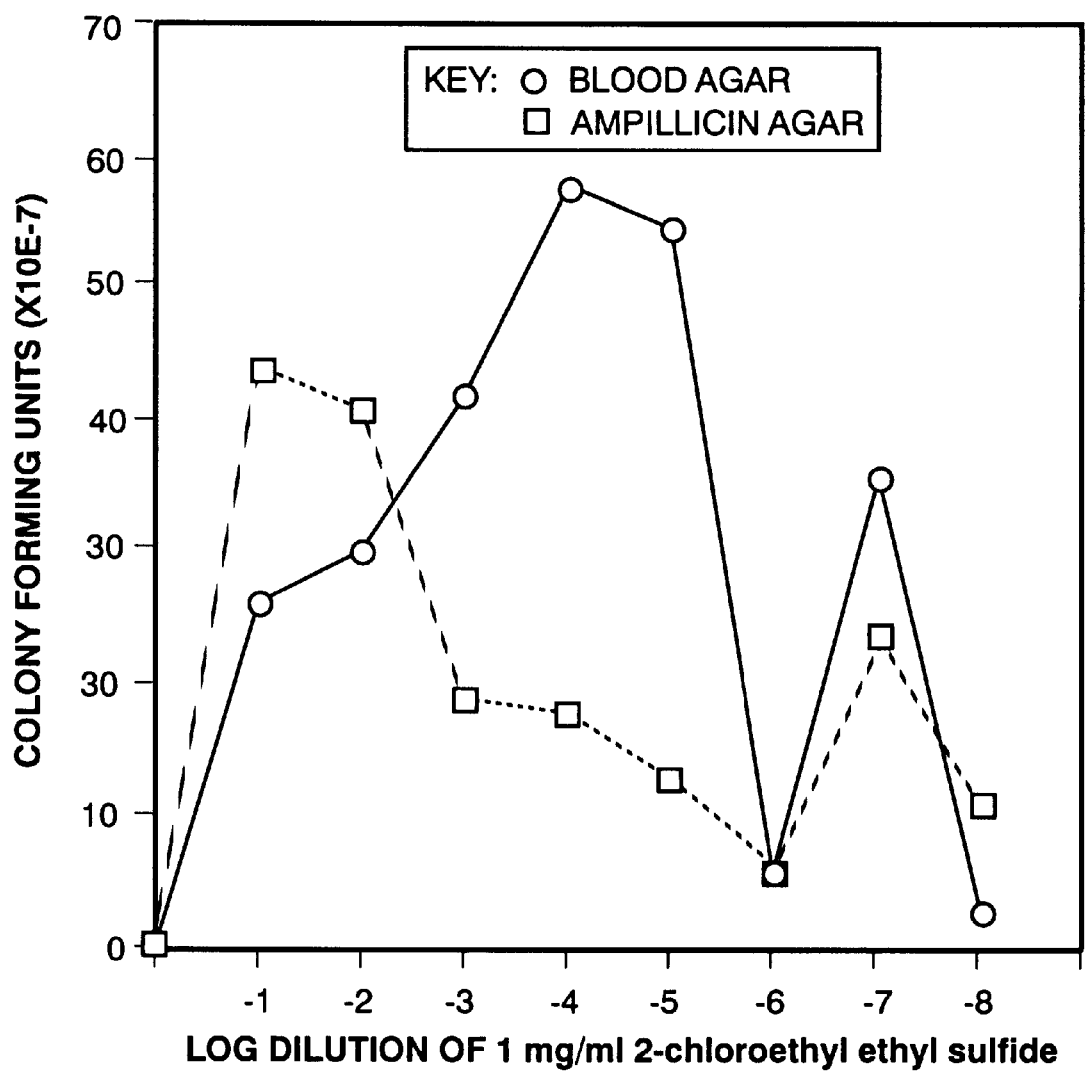
Figure 10:
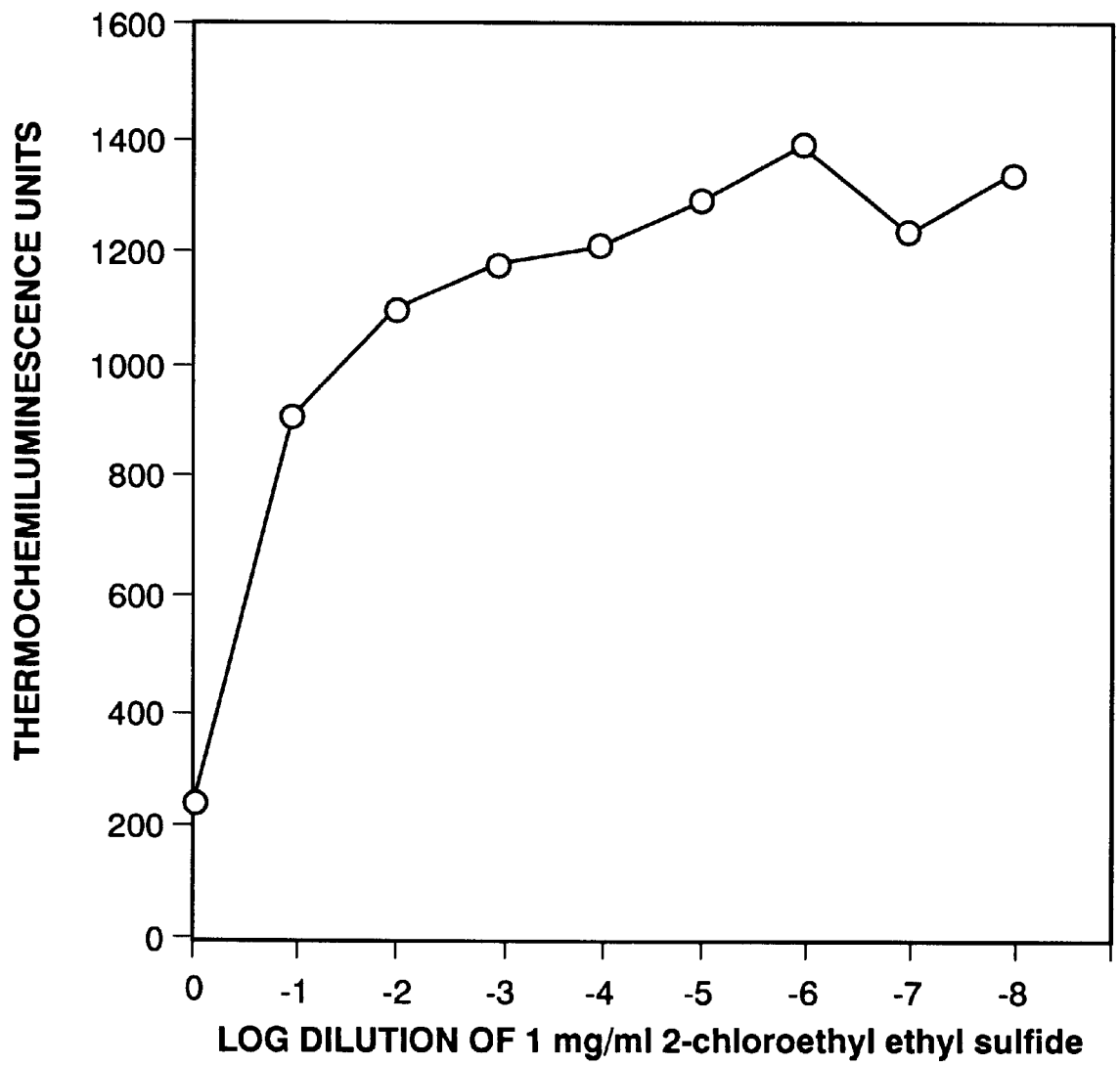

The JM109/pIC20RNR1.1 *E. coli* can be employed for mutagenic assay, as shown in FIGS. 8–10. The 3AT medium with 0.4% mannitol added, containing the indicated dilution of the half-mustard 2-chloroethyl ethyl sulfide (a weak mutagen that is used as a chemical warfare mustard simulant) was inoculated and cultured for 24 hours. The 3AT culture was then used to inoculate solid medium, blood agar or LB agar containing ampicillin (30 $\mu$g/ml), to isolate and count surviving colonies after another 24 hours of incubation.

FIG. 8 shows the colony counts for an initial inoculation of a billion microorganisms on blood agar (○) and ampicillin agar (□) for different concentrations of the half-mustard. The increased counts with increased dilution indicated an increase in mutants and a decrease in lethality with increased dilutions. FIG. 9 shows the colony counts for an initial inoculation of 10 million microorganisms on blood agar (○) and ampicillin agar (□) for different concentrations of the half-mustard. The survival curves indicate optima half-mustard concentrations for mutation. The $10^{-7}$ dilution maxima are spurious to the half-mustard (spontaneous mutations). The separate maxima for blood agar (B) and ampicillin agar (A) indicate the probability of mutating three genes in effect on survival vs. a single gene (the introduced barley nitrate reductase gene fragment). FIG. 10 shows the thermochemiluminescence (addition of peroxide, sodium bicarbonate and 42° C.) for samples taken from 24 hr samples of the 10 million bacteria experiment, reflect the increased survival with increased dilution of the half-mustard, but reaches a maximum for further dilutions. This is the result of increased DALM formation per microorganism, this keeping the total thermochemiluminescence constant even though the number of surviving bacteria decrease with increased dilution of the half-mustard. The maxima effects shown in FIGS. 9 and 10 are the result of the double-lethal effect in the 3AT medium. The colonies will either not grow or die off early in the culture if the DALM substrates cannot be used; if they are used (by the recombinant DNA bacteria) the bacteria will die later (after about 6 hours) due to the overt formation of toxic DALM.

Thus, it can be seen that the *E. coli* JM109/pIC20RNR1.1 can be employed for the detection of physical, chemical and/or radiation stressors. Physical stressors, such as increased temperature, can be assayed by growing the cells on 3AT medium, counting the thus-incubated cells, subjecting the cells to increased temperature for short periods, plating the thus-subjected cells, and counting the survivors. Chemical stressors, such as mutagens, can be assayed by growing the cells on 3AT medium containing the mutagen, plating the thus-incubated cells on blood agar or LB ampicillin plates, counting the surviving cells, and comparing the surviving count to that of a known mutagen. For the assay of radiation stressors, the cells are grown in 3AT medium, exposed to the stressor, plated, counted and the count compared to a known stressor.

The processes of this invention do not require dangerous and difficult to handle organic solvents. These processes can be operated on a large scale with a nonpathogenic bacteria. In situ labeling of nucleic acids and proteins can be accomplished without further organic chemical manipulation. Unlike other immunoassay or ligand-antiligand tests, dead organisms are not detected since only metabolizing organisms can produce DM or DALM.

Various modifications of the present invention can be made in view of the foregoing disclosure without departing from the spirit and scope of the invention.

We claim:

1. A method for producing diazoluminomelanin (DALM) which comprises culturing in a medium containing nitrate, 3-amino-L-tyrosine (3-AT) and luminol under suitable metabolic conditions, the microorganism JM109/pIC20RNR1.1.

2. A method for the assay of a chemical stressor which comprises the steps, in sequence, of:
   (a) incubating *E. coli* JM109/pIC20RNR1.1 in a 3AT broth containing 0.4% mannitol and a known quantity of said stressor;
   (b) plating the incubated cells;
   (c) counting surviving colonies; and
   (d) comparing the surviving count with the survival count of a known stressor.

3. A method for the assay of exposure to radiation which comprises the steps, in sequence, of:
   (a) incubating *E. coli* JM109/pIC20RNR1.1 in a 3AT broth;
   (b) washing the incubated cells and placing the washed cells in trypticase soy broth with sodium bicarbonate and hydrogen peroxide;
   (c) exposing the cells from step (b) to a radiation source;
   (d) plating the cells after exposure;
   (e) counting surviving colonies; and
   (f) comparing the surviving count with the survival count of a known exposure.

* * * * *